(12) United States Patent
Frikart et al.

(10) Patent No.: US 8,533,475 B2
(45) Date of Patent: Sep. 10, 2013

(54) METHOD FOR PAIRING AND AUTHENTICATING ONE OR MORE MEDICAL DEVICES AND ONE OR MORE REMOTE ELECTRONIC DEVICES

(75) Inventors: Marcel Frikart, Bern (CH); Markus Oberli, Kirchberg (CH); Philippe Frikart, Grosshoechstetten (CH); Raymond Strickland, Indianapolis, IN (US); Markus Jungen, Bolligen (CH); Matthias Ehrsam, Bolligen (CH); Christian Frey, Niedergoesgen (CH); Felix Lindner, Berlin (DE)

(73) Assignees: Roche Diagnostics Operations, Inc., Indianapolis, IN (US); Roche Diagnostics International AG, Rotkreuz (CH)

( * ) Notice: Subject to any disclaimer, the term of this patent is extended or adjusted under 35 U.S.C. 154(b) by 497 days.

(21) Appl. No.: 12/632,601

(22) Filed: Dec. 7, 2009

(65) Prior Publication Data

US 2010/0115279 A1 May 6, 2010

Related U.S. Application Data (63) Continuation of application No. PCT/US2008/066247, filed on Jun. 9, 2008.

(60) Provisional application No. 60/937,779, filed on Jun. 29, 2007, provisional application No. 60/937,933, filed on Jun. 29, 2007.

(30) Foreign Application Priority Data

Jun. 8, 2007 (EP) .................................... 07011313

(51) Int. Cl.
*H04L 9/32* (2006.01)

(52) U.S. Cl.
USPC ........... 713/171; 713/169; 713/170; 455/41.2

(58) Field of Classification Search
USPC .................................. 713/169–172; 455/41.2
See application file for complete search history.

(56) References Cited

U.S. PATENT DOCUMENTS

| 4,146,029 | A | 3/1979 | Ellinwood, Jr. |
| 5,291,609 | A | 3/1994 | Herz |

(Continued)

FOREIGN PATENT DOCUMENTS

| EP | 0079405 A1 | 5/1983 |
| EP | 0290683 A2 | 11/1988 |

(Continued)

OTHER PUBLICATIONS

Levy, M., et al., "Fifo Memories Supply the Glue for High-Speed Systems", EDN Eleectrical Design News, Reed Business Information, Highlands Ranch, Co, US, vol. 42, No. 6, Mar. 14, 1997, pp. 65, 66, 68 and 70. XP 000695233.

(Continued)

*Primary Examiner* — Harunur Rashid
(74) *Attorney, Agent, or Firm* — Roche Diagnostics Operations, Inc.

(57) ABSTRACT

A method for authenticating a medical device and a remote electronic device may include generating a PIN code by one device, capturing the generated PIN code with the other device, checking authentication of the PIN code, which is based at least in part on the captured PIN code, by the one device, generating a strong key by the one device, sending the strong key encrypted to the other device, checking authentication of the sent strong key by the one device, and upon successful authentication, storing the strong key in a memory of the one device and the other device. The roles of the medical device and the remote electronic device may be reversed in the authenticating method. The authenticating method may be preceded by a pairing process and/or followed by a binding process.

1 Claim, 4 Drawing Sheets

(56) References Cited

U.S. PATENT DOCUMENTS

| | | | |
|---|---|---|---|
| 5,364,346 | A | 11/1994 | Schrezenmeir |
| 5,748,103 | A | 5/1998 | Flach et al. |
| 5,997,475 | A | 12/1999 | Bortz |
| 6,289,421 | B1 | 9/2001 | Ali et al. |
| 6,668,196 | B1 | 12/2003 | Villegas et al. |
| 6,772,331 | B1 * | 8/2004 | Hind et al. ............... 713/151 |
| 6,909,439 | B1 | 6/2005 | Amro et al. |
| 2001/0044731 | A1 | 11/2001 | Coffman et al. |
| 2004/0078416 | A1 | 4/2004 | Kawasaki et al. |
| 2004/0187001 | A1 * | 9/2004 | Bousis ..................... 713/175 |
| 2004/0248840 | A1 | 12/2004 | Hansen et al. |
| 2005/0091577 | A1 | 4/2005 | Torres et al. |
| 2005/0162395 | A1 | 7/2005 | Unruh |
| 2006/0047192 | A1 | 3/2006 | Hellwig et al. |
| 2006/0068760 | A1 * | 3/2006 | Hameed et al. ............ 455/41.1 |
| 2006/0135065 | A1 * | 6/2006 | Lee et al. .................. 455/41.1 |
| 2006/0173406 | A1 | 8/2006 | Hayes et al. |
| 2006/0217061 | A1 | 9/2006 | Steele et al. |
| 2007/0109325 | A1 | 5/2007 | Eveleigh |
| 2007/0142767 | A1 | 6/2007 | Frikart et al. |

FOREIGN PATENT DOCUMENTS

| | | |
|---|---|---|
| EP | 1759726 A2 | 3/2007 |
| EP | 1788501 A1 | 5/2007 |
| EP | 1795116 A1 | 6/2007 |
| WO | 00/48112 A2 | 8/2000 |
| WO | 2004/099898 A2 | 11/2004 |
| WO | 2006/032653 A2 | 3/2006 |
| WO | 2006/046015 A1 | 5/2006 |
| WO | 2006/108304 A1 | 10/2006 |

OTHER PUBLICATIONS

Hastings, C., et al., "Future Trends in Fifo Architectures", Wescon Technical Papers, Western Periodicals Co., North Hollywood, CA, USA, vol. 36, Nov. 17, 1992, pp. 174-178. XP 000350089.

Rasid, M. F. A., et al., "Bluetooth Telemedicine Processor for Multichannel Biomedical Signal Transmission via Mobile Cellular Netowrks", IEEE Transactions on Information Technology in Biomedicine, IEEE Service Center, Los Alamitos, CA, USA, vol. 9, No. 1, Mar. 1, 2005, pp. 35-43. XP 011127538.

International Search Report and Written Opinion mailed Oct. 30, 2008 from PCT/US2008/066288.

International Search Report and Written Opinion mailed Dec. 22, 2008 from PCT/US2008/066267.

International Search Report and Written Opinion mailed Jan. 9, 2009 from PCT/US2008/066248.

International Search Report and Written Opinion mailed Dec. 22, 2008 from PCT/US2008/066299.

International Search Report and Written Opinion mailed Jan. 14, 2009 from PCT/US2008/066331.

International Search Report and Written Opinion mailed Jan. 14, 2009 from PCT/US2008/066262.

The Bluetooth Forum: "Bluetooth security", Internet citation [online], Feb. 22, 2001. XP002171382. http://www.bluetooth.com/developer/specifiction/specification.asp.

Gehrmann, Christian, "Bluetooth Security White Paper, Bluetooth SIG", Bluetooth Doc, Apr. 19, 2002, pp. 1-46. XP003010085.

International Search Report mailed Jul. 24, 2008 from corresponding PCT case.

* cited by examiner

METHOD FOR PAIRING AND AUTHENTICATING ONE OR MORE MEDICAL DEVICES AND ONE OR MORE REMOTE ELECTRONIC DEVICES

REFERENCE

This application is a continuation of PCT/US 2008/066247 filed Jun. 9, 2008 which is based on and claims priority to European Patent Application Ser. No. 07011313, filed Jun. 8, 2007, U.S. Provisional Patent. Application Ser. No. 60/937,779, filed Jun. 29, 2007, and U.S. Provisional Patent Application Ser. No. 60/937,933, filed Jun. 29, 2007, which are all hereby incorporated by reference.

FIELD

This disclosure relates generally to medical devices configured to wirelessly communicate with remote electronic devices, and more specifically to pairing and authenticating one or more medical devices and one or more remote devices for subsequent secure wireless communications.

BACKGROUND

It is generally known to provide for wireless communications between a medical device, such as an ambulatory medical device, and a remote electronic device. It is desirable with such arrangements to configure the medical device and the remote electronic device in a manner that provides for secure wireless communications between the two devices. It is further desirable in systems that may include a plurality of medical devices and/or a plurality of remote electronic devices to configure one or more of the medical devices and one or more of the remote electronic devices in a manner that provides for secure wireless communications between various combinations of the devices.

SUMMARY

The present invention may comprise one or more of the features recited in the attached claims, and/or one or more of the following features and combinations thereof. A method for authenticating a medical device and a remote electronic device that are placed in communication range relative to each other may comprise generating at least a portion of a PIN code by one of the medical device and the remote electronic device, capturing the at least a portion of the generated PIN code with the other of the medical device and the remote electronic device, checking authentication of the PIN code, which is based at least in part on the captured at least a portion of the generated PIN code, by the one of the medical device and the remote electronic device, generating at least one strong key by one of the medical device and the remote electronic device, sending the at least one strong key encrypted to the other of the medical device and the remote electronic device, checking authentication of the sent at least one strong key by the one of the medical device and the remote electronic device, and upon successful authentication of the PIN code and the at least one strong key, storing the at least one strong key in a memory of the medical device and in a memory of the remote electronic device.

In one illustrative embodiment, generating at least a portion of a PIN code may comprise generating a complete PIN code by the one of the medical device and the remote electronic device. Capturing the at least a portion of the generated PIN code comprises capturing the complete PIN code with the other of the medical device and the remote electronic device. Checking authentication of the PIN code comprises checking authentication of the captured complete PIN code by the one of the medical device and the remote electronic device. In an alternate embodiment, the method may further comprise generating at least another portion of the PIN code by the other of the medical device and the remote electronic device, and forming by the other of the medical device and the remote electronic device a complete PIN code based on the at least a portion of the PIN code and the at least another portion of the PIN code. In this embodiment, checking authentication of the PIN code may comprise checking authentication of the complete PIN code by the one of the medical device and the remote electronic device.

In one illustrative embodiment, capturing the at least a portion of the generated PIN code may comprise displaying the at least a portion of the generated PIN code by the one of the medical device and the remote electronic device, and instructing via a display of the other of the medical device and the remote electronic device manual input of the at least a portion of the generated PIN code into the other of the medical device and the remote electronic device. In an alternative embodiment, capturing the at least a portion of the generated PIN code may comprise one of sending the at least a portion of the generated PIN code by the one of the medical device and the remote electronic device to the other of the medical device and the remote electronic device and retrieving the at least a portion of the generated PIN code by the other of the medical device and the remote electronic device from the one of the medical device and the remote electronic device.

The method may further comprise exchanging respective device identification codes between the medical device and the remote electronic device. The respective device identification codes may, for example, be exchanged between the medical device and the remote electronic device following authentication of the at least one strong key.

Upon non-successful authentication of either of the PIN code and the at least one strong key, in one illustrative embodiment, the method may return to the step of generating at least a portion of a PIN code by one of the medical device and the remote electronic device. In an alternative embodiment, a message may be displayed on at least one of the medical device and the remote electronic device indicating that the authentication was not successful and the method may return to the step of displaying the at least a portion of the generated PIN code by the one of the medical device and the remote electronic device, upon non-successful authentication of either of the PIN code and the at least one strong key.

The method may further comprise restarting the other of the medical device and the remote electronic device upon successful authentication of the PIN code and the at least one strong key.

The method may further comprise performing a pairing phase prior to executing any of the steps of the method for authenticating. In one illustrative embodiment, the pairing phase may comprise setting the other of the medical device and the remote electronic device in a pairable mode in order to be discoverable by the one of the medical device and the remote electronic device, setting the one of the medical device and the remote electronic device in a pairing mode, performing a device discovery inquiry by the one of the medical device and the remote electronic device, displaying discovered devices resulting from the device discovery inquiry, upon user selection from the displayed discovered devices of the other of the medical device and the remote electronic device, pairing the one of the medical device and the remote electronic device with the other of the medical device and the remote electronic device, upon successful pairing generating a link key on the medical device and on the remote electronic device, storing the link key and a virtual address of the other of the medical device and the remote electronic device in a memory of the one of the medical device and the remote electronic device, and storing the link key and a virtual address of the one of the medical device and the remote electronic device in a memory of the other of the medical device and the remote electronic device, and connecting the medical device and the remote electronic device together.

In one illustrative embodiment, BlueTooth® may be used as a communication protocol for communication between the medical device and the remote electronic device during the pairing phase.

The method may further comprise filtering discovered devices resulting from the device discovery inquiry prior to displaying the discovered devices such that only discovered devices that are in the pairable mode are displayed for user selection. Alternatively or additionally, the method may further comprise filtering discovered devices resulting from the device discovery inquiry prior to displaying the discovered devices by comparing the discovered devices to entries of a predefined device list and displaying only the discovered devices that match entries on the predefined device list.

The method may further comprise requesting authentication of the other of the medical device and the remote electronic device selected from the displayed discoverable devices. For such authentication, the one of the medical device and the remote electronic device and the other of the medical device and the remote electronic device may each provide a fixed PIN code.

The method may further comprise performing a binding phase after executing all of the steps of the method for authenticating. The binding phase may comprise sending service versions of all operating modes of the remote electronic device by one of the medical device and the remote electronic device to the other of the medical device and the remote electronic device, upon a determination by the other of the medical device and the remote electronic device that the sent service versions are compatible with corresponding service versions stored in the memory of the other of the medical device and the remote electronic device, storing a pass flag in a memory of the medical device and in a memory of the remote electronic device, and upon a determination by the other of the medical device and the remote electronic device that at least one of the sent service versions is not compatible with a corresponding one of the service versions stored in the memory of the other of the medical device and the remote electronic device, removing the at least one strong key from the memory of the medical device and from the memory of the remote electronic device.

A method may be provided for pairing a medical device and a remote electronic device that are placed in communication range relative to each other. The method may comprise setting one of the medical device and the remote electronic device in a pairing mode, performing a device discovery inquiry by the other of the medical device and the remote electronic device, displaying discovered devices resulting from the device discovery inquiry, upon user selection from the displayed discovered devices of the one of the medical device and the remote electronic device, pairing the other of the medical device and the remote electronic device with the one of the medical device and the remote electronic device, upon successful pairing generating a link key on the medical device and on the remote electronic device, storing the link key and a virtual address of the one of the medical device and the remote electronic device in a memory of the other of the medical device and the remote electronic device, and storing the link key and a virtual address of the other of the medical device and the remote electronic device in a memory of the one of the medical device and the remote electronic device, and connecting the medical device and the remote electronic device together.

Illustratively, BlueTooth® may be used as a communication protocol for communication between the medical device and the remote electronic device.

The method may further comprise filtering discovered devices resulting from the device discovery inquiry prior to displaying the discovered devices such that only discovered devices that are in the pairable mode are displayed for user selection. Alternatively or additionally, the method may further comprise filtering discovered devices resulting from the device discovery inquiry prior to displaying the discovered devices by comparing the discovered devices to entries of a predefined device list and displaying only the discovered devices that match entries on the predefined device list.

The method may further comprise requesting authentication of the one of the medical device and the remote electronic device selected from the displayed discoverable devices. For such authentication, the one of the medical device and the remote electronic device and the other of the medical device and the remote electronic device may each provide a fixed PIN code.

A method may be provided for binding a medical device and a remote electronic device that are placed in communication range relative to each other. The method may comprise sending service versions of all operating modes of the remote electronic device by one of the medical device and the remote electronic device to the other of the medical device and the remote electronic device, upon a determination by the other of the medical device and the remote electronic device that the sent service versions are compatible with corresponding service versions stored in the memory of the other of the medical device and the remote electronic device, storing a pass flag in a memory of the medical device and in a memory of the remote electronic device, and upon a determination by the other of the medical device and the remote electronic device that at least one of the sent service versions is not compatible with a corresponding one of the service versions stored in the memory of the other of the medical device and the remote electronic device, removing the at least one strong key from the memory of the medical device and from the memory of the remote electronic device.

DETAILED DESCRIPTION

For the purposes of promoting an understanding of the principles of the invention, reference will now be made to a number of illustrative embodiments shown in the attached drawings and specific language will be used to describe the same.

The following co-pending patent applications are incorporated herein by reference: PCT Patent Application No. PCT/US 2008/066288, entitled APPARATUS AND METHOD FOR REMOTELY CONTROLLING AN AMBULATORY MEDICAL DEVICE, PCT Patent Application No. PCT/US 2008/066262, entitled COMBINATION COMMUNICATION DEVICE AND MEDICAL DEVICE FOR COMMUNICATING WIRELESSLY WITH A REMOTE MEDICAL DEVICE, PCT Patent Application No. PCT/US 2008/066331, entitled METHOD AND APPARATUS FOR DETERMINING AND DELIVERING A DRUG BOLUS, PCT Patent Application No. PCT/US 2008/066267, entitled LIQUID INFUSION PUMP, PCT Patent Application No. PCT/US 2008/066299, entitled USER INTERFACE FEATURES FOR AN ELECTRONIC DEVICE, PCT Patent Application No. PCT/US 2008/066248, entitled DEVICE AND METHODS FOR OPTIMIZING COMMUNICATIONS BETWEEN A MEDICAL DEVICE AND A REMOTE ELECTRONIC DEVICE, and U.S. Provisional Patent Application Ser. No. 61/130,855, entitled DEVICE AND METHODS FOR OPTIMIZING COMMUNICATIONS BETWEEN AN ELECTRONIC DEVICE AND A MEDICAL DEVICE.

Figure 1:
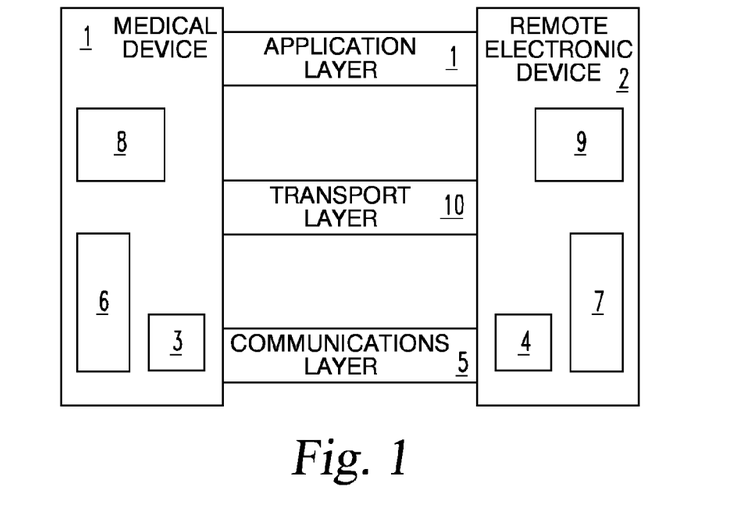
FIG. 1 shows a diagram of one illustrative embodiment of an abstract interconnection layer model for wireless communications between a medical device and a remote electronic device.

Referring now to FIG. 1, a medical device 1 and a remote electronic device 2 are shown along with one illustrative embodiment of an abstract interconnection layer model for wireless communications between the two devices 1 and 2. The medical device 1 may be, for example, an ambulatory medical device, although the medical device 1 may alternatively be or include a non-ambulatory medical device. Examples of such an ambulatory medical device 1 may include, but should not be limited to, one or any combination of a medication delivery device such as an infusion pump, a glucose meter, a body fluid analyte sensor system including one or more subcutaneous and/or implanted body fluid analyte sensors, a remote terminal representing a remote infusion pump display on which data from the infusion pump is displayed to a user, or the like. The remote electronic device 2 may be or include, but should not be limited to, a conventional personal data assistant (PDA) device, an application specific remote electronic device that may be hand-held, attachable or mountable to clothing, configured to be worn by a person such as on or about a limb or portion thereof, on or about a head or portion thereof, or on or about a body or portion thereof, attachable to a key ring, or the like, a portable wireless communication device with an on-board glucose meter, a smart phone, a personal computer (PC), a laptop, notebook or similar computer, or the like. In one specific embodiment, which should not be considered to be limiting in any way, the medical device 1 is an insulin infusion pump and the remote electronic device is a hand-held, diabetes management unit. The functionality of the medical device 1 and the remote electronic device 2 may also be reversed, i.e., the medical device 1 may be one of the above devices mentioned as examples for a remote electronic device 2 and the remote electronic device 2 may be one of the above devices mentioned as examples for a medical device 1.

In the illustrated embodiment, the medical device 1 includes a wireless communication module 3 and the remote electronic device 2 also includes a wireless communication module 4. The wireless communication modules 3 and 4 communicate with each other wirelessly via a communications layer 5. The wireless communication modules 3 and 4 each include a dedicated conventional processor connected to a conventional wireless transmitter and a conventional wireless receiver, or to a conventional wireless transceiver. The wireless communication modules 3 and 4 are illustratively configured to communicate with each other using any conventional wireless medium including, for example, but not limited to radio frequency (RF), infrared (IR), microwave, inductive coupling, or the like. The communications layer 5 may likewise be any conventional communications layer that supports the chosen wireless medium. In one specific example, which should not be considered limiting in any way, the communication modules 3 and 4 are each configured to communicate via RF according to conventional a BlueTooth® radio frequency communications protocol, and the communications layer 5 is accordingly a conventional BlueTooth® communications layer through which the communication modules 3 and 4 may communicate.

The medical device 1 and the remote electronic device 2 each further include a conventional control unit 6 and 7 respectively. Illustratively, the control units 6 and 7 may be or include a conventional microprocessor, although either or both of the control units 6 and 7 may alternatively include other conventional control circuits. The medical device 1 and the remote electronic device 2 each further include a user interface 8 and 9 respectively. Illustratively, the user interfaces 8 and 9 are conventional visual display units, each of which may be or include a conventional liquid crystal display (LCD), one or more light emitting diodes (LEDs), a vacuum fluorescent display or the like, although this disclosure contemplates embodiments in which either or both of the user interfaces are or include a conventional audible device configured to be responsive to one or more control signals to produce one or more audible sounds, a conventional tactile device configured to be responsive to one or more control signals to produce a tactile signal that may be perceived, i.e., felt, by a person near or in contact with the device carrying the tactile device, and the like.

To provide for secure communications between the medical device 1 and the remote electronic device 2, the medical device 1 and the remote electronic device 2 are mutually authenticated according to a process that will be referred to herein as pairing and authentication. In embodiments in which the wireless communication modules 3 and 4 are BlueTooth® communication modules as described above, the pairing and authentication process illustratively includes three phases: (1) pairing, (2) authentication and (3) binding. In this embodiment, the pairing and authentication process, as will be described hereinafter, will be considered successful only after all three of the phases are consecutively and successfully executed. In alternate embodiments, however, it will be understood that not all three phases of the above-described pairing and authentication process may be required. For example, in some embodiments the binding process may be omitted, and the pairing and authentication process may include only the first two phases. In certain other embodiments in which the wireless communication modules 3 and 4 are not BlueTooth® communication modules, the pairing process may be omitted and/or the binding phase may be omitted, in which case the pairing and authentication process may include only the second and third phases, the first and second phases or in some cases just the second phase. Those skilled in the art will recognize that the number and combination of the three phases of the pairing and authentication process that may be used will typically be dictated by the particular application and will depend, at least to some extent, on the desired level of security with which successfully paired and authenticated devices will thereafter communicate. While the remainder of this disclosure will describe a system in which successful completion of all three phases of the pairing and authentication process are required, it will be understood that in alternate embodiments successful execution of fewer and different combinations of the three phases may alternatively define successful completion of the pairing and authentication process as just described.

The pairing phase of the pairing and authentication process takes place between the medical device 1 and the remote electronic device 2 via the communication layer 3 as described above. In the pairing phase, a trusted relationship between the medical device 1 and the remote electronic device 2 is established as will be described in detail hereinafter. Following successful pairing according to the pairing phase, the medical device 1 and the remote electronic device 2 are wirelessly connected by a security and transport layer 10. Physically, the security and transport layer 10 may form a single layer as illustrated in FIG. 1, or may instead be partitioned into a security layer and a separate transport layer.

In either case, the authentication phase of the pairing and authentication process takes place between the medical device 1 and the remote electronic device 2 via the security portion of the security and transport layer 10. When the pairing and authentication process is successfully completed and the medical device 1 and the remote electronic device 2 thereafter communicate wirelessly in a secure manner, the transport portion of the security and transport layer 10 is illustratively used for error recognition and retransmission of data. Following successful authentication according to the authentication phase, a secure link is established between the medical device 1 and the remote electronic device 2, and data can be transmitted between the two devices 1 and 2 via an application layer 11.

The binding phase of the pairing and authentication process takes place between the medical device 1 and the remote electronic device 2 via the application layer 11. Following successful completion of the binding phase, the pairing and authentication process is complete, and the medical device 1 and the remote electronic device 2 may thereafter communicate wirelessly in a secure manner. Secure transmission of data between the medical device 1 and the remote electronic device 2 does not occur until a secure data transmission link is established according to the pairing and authentication process just described.

Figure 2:
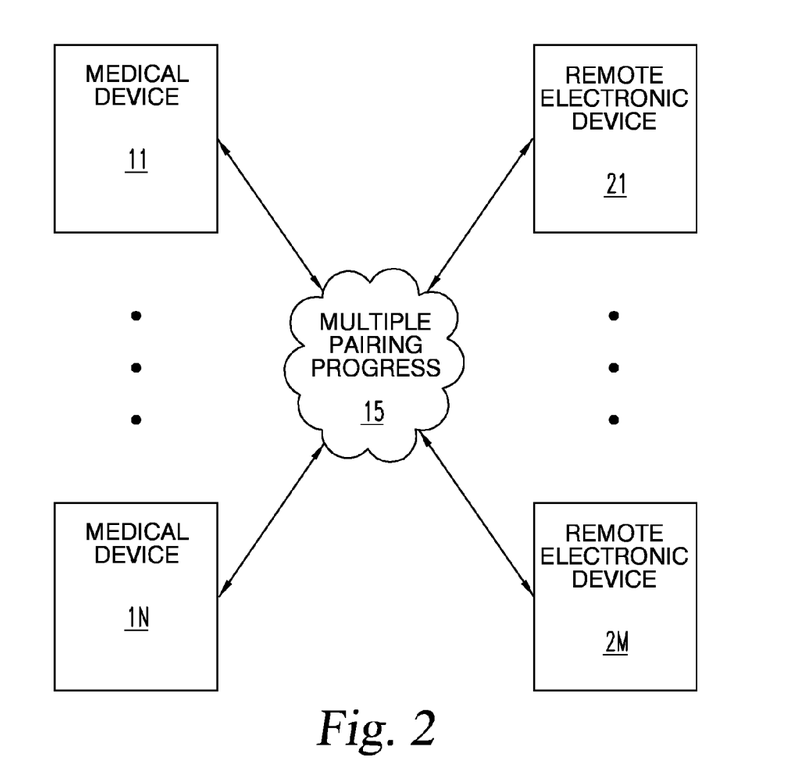
FIG. 2 shows a diagram illustrating pairing and authentication carried out between one or more medical devices and one or more other medical devices and/or one or more remote electronic devices.

In the embodiment illustrated and described with respect to FIG. 1, the pairing and authentication process is carried out between only one medical device and one remote electronic device 2 to provide for secure wireless communication between only the two devices 1 and 2. In alternative embodiments, as illustrated by example in FIG. 2, the medical device communication system may include any number, N, of medical devices, $1_1\text{-}1_N$, where N may be any positive integer, and any number, M, of remote electronic devices, $2_1\text{-}2_M$, where M may be any positive integer. In this embodiment, a multiple pairing process 15 is supported in which a single one of the medical devices $1_J$ (J=1 to N) may be paired and authenticated with any one or more of the M remote electronic devices, $2_1\text{-}2_M$, and/or with one or more of the remaining N-1 medical devices, $1_1\text{-}1_N$, a single one of the remote devices $1_K$ (K=1 to M) may be paired and authenticated with any one or more of the N medical devices and/or with one or more of the remaining M-1 remote electronic devices, $2_1\text{-}2_M$, any subset of the plurality of medical devices, $1_1\text{-}1_N$, may be paired and authenticated with any subset of the plurality of remote electronic devices, $2_1\text{-}2_M$ and/or with one or more of the remaining medical devices, $1_1\text{-}1_N$, or any subset of the plurality of remote electronic devices, $2_1\text{-}2_M$, may be paired and authenticated with any subset of the plurality of medical devices, $1_1\text{-}1_N$ and/or with one or more of the remaining remote electronic devices, $2_1\text{-}2_M$. Using this extended approach, a medical device communication system may be established in which one or more medical devices, $1_1\text{-}1_N$, may be configured for secure communications with one or more remote electronic devices, $2_1\text{-}2_M$ and/or with any one or more of the remaining medical devices, $1_1\text{-}1_N$.

Figure 3:
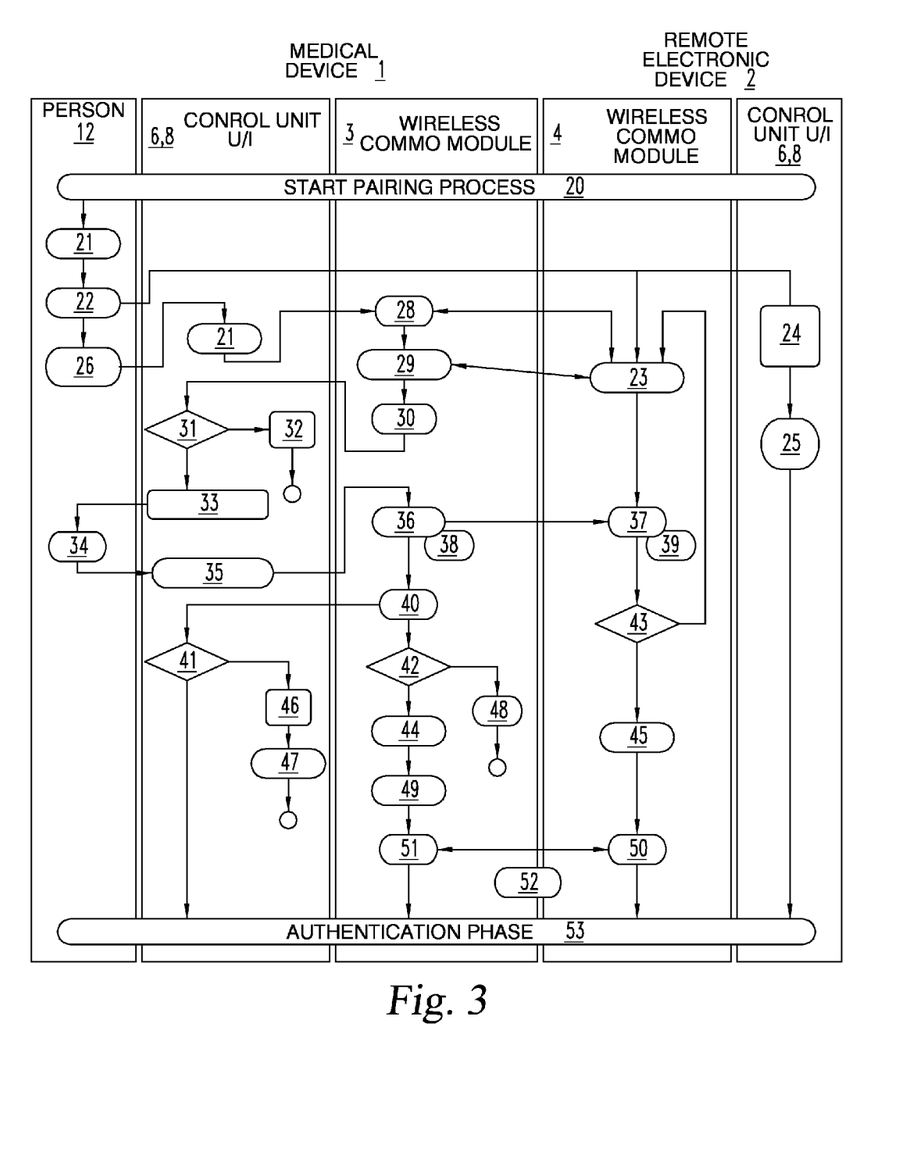
FIG. 3 shows a flowchart of one illustrative embodiment of a pairing process for pairing a medical device with a remote electronic device.

Referring now to FIG. 3, a flowchart is shown of one illustrative embodiment of a pairing process for pairing a medical device 1 with a remote electronic device 2. Although the pairing process is illustrated and will be described in the context of a single medical device 1 and a single remote electronic device 2, it will be understood that the pairing process of FIG. 3 may be carried out between one or more medical devices and one or more remote electronic devices, between one or more medical devices and one or more other medical devices, and/or between one or more remote electronic devices and one or more other remote electronic devices. In any case, the flowchart of FIG. 3 is partitioned into the various entities and device/electrical components that carry out the various acts of the pairing process. Thus, for example, a person 12 conducting the pairing process will carry out some of the acts, the control unit 6 of the medical device 1 will carry out some of the acts with the aid of the user interface 8, the communications module 3 of the medical device 1 will carry out some of the acts, the communications module 4 of the remote electronic device 2 will carry out some of the acts and the control unit 7 of the remote electronic device 2 will carry out some of the acts with the aid of the user interface 9.

Illustratively, a precondition for the pairing process of FIG. 3, in embodiments in which the pairing and authentication process may be carried out only between a single medical device 1 and a single remote electronic device 2, is that on the side of the medical device 1 no remote electronic device 2 is currently paired. Step 20 denotes the start of the pairing process, and thereafter at step 21 the medical device 1 and the remote device 2 are placed in range relative to each other by a user 12 for wireless communication and connection, although this disclosure contemplates embodiments in which the pairing process and/or the subsequent authentication process and/or the subsequent binding process may be carried out, at least in part, via a wired connection and/or via an alternate wireless connection, i.e., other than via the communication modules 3 and 4.

In step 22 the remote electronic device 2 is set into pairable mode, which begins the pairing phase. The pairing phase is illustratively optional, and this disclosure accordingly contemplates embodiments in which the pairing phase is omitted from the overall pairing and authenticating process. In any case, the user 12 illustratively sets the remote electronic device 2 into pairable mode by pressing a specific key, a combination of keys or a specified sequence of keys on the remote device 2 on power up, or by entering a specific key, a combination of keys or sequence of keys or entering a specific pairing menu, after power up. Pressing the specific key or keys activates a specific pairing firmware on the communication module 4 as well as on the control unit 7 of the remote electronic device 2. The communication module 4 then sets the remote electronic device 2 in step 23 in pairable mode, i.e., in the mode of being device inquirable and connectable, in order to be discoverable by the medical device 1. At step 24, the control unit 7 illustratively (and optionally) controls the user interface 9 of the remote device 2 to display a message indicating that the pairing process, or that the pairing and authentication process, has begun, e.g., a message such as "Starting Pairing and Authentication Process" or a similar message. Thereafter at step 25, the control unit 7 of the remote electronic device 2 attempts to communicate with the medical device 1 via the transport portion of the security and transport layer 10. Communication via the transport portion of the security and transport layer 10 will, however, not be possible until successful completion of the pairing phase, i.e., upon successful pairing of the communication modules 3, 4 of the medical device 1 and the remote electronic device 2.

In step 26 the medical device 1 is set into pairing mode. Illustratively, the user 12 sets the medical device 1 into the pairing mode by selecting a corresponding pairing menu which is displayed on the user interface 8 of the medical device 1 under the control of the control unit 6, or by pressing a specific key, a combination of keys or a specified sequence of keys on the medical device 1. The control unit 6 of the medical device 1 then starts the actual pairing process in step 27 and instructs the communication module 3 of the medical device 1 in step 28 to initiate and perform a remote device discovery inquiry. In one illustrative embodiment, the communication module 3 searches during the remote device discovery inquiry for potential pairable remote electronic devices 2 in range, and obtaining in the process the virtual addresses of the communication modules 4 of any remote electronic devices 2 in range. In step 29 the discovered remote electronic devices 2 are illustratively filtered in one embodiment so that only pairable remote electronic devices 2, i.e., remote electronic devices 2 that are set in the pairable mode, are found. Alternatively or additionally, the discovered remote electronic devices may be filtered such that only devices with a special configuration, e.g., a special address, a friendly or service name, that offers a special service(s), etc., are found. In any case, other electronic devices, which are not aimed at being connected with the medical device 1, can be filtered out. In step 30 the communication module 3 sends the found remote electronic devices 2, i.e., the virtual or special address, friendly name, service name, special service(s), etc., of the found remote electronic devices 2, to the control unit 6 of the medical device 1.

The control unit 6 of the medical device 1 checks in step 31 if any remote electronic devices 2 have been found during the remote device discovery inquiry of steps 28-30. If no remote electronic devices 2 have been found, the control unit 6 illustratively controls the user interface 8 of the medical device 1 to display in step 32 a message indicating that no remote electronic devices were found during the remote device discovery inquiry, e.g., a message such as "No remote devices found" or a similar message. With no remote devices to pair with, the pairing process then ends. If, on the other hand, one or more remote electronic devices 2 have been found during the remote device discovery inquiry, the control unit 6 then controls the user interface 8 of the medical device 1 at step 33 to display the one or more discovered, pairable remote electronic devices 2 as a list on the user interface 8. Illustratively, although not necessarily, friendly names of the found remote electronic devices 2 are displayed on the user interface 8 at step 33, wherein the such friendly names may contain, in whole or in part, the serial numbers or other identification codes of the discovered remote electronic devices 2.

Thereafter in step 34, the user 12 selects a remote electronic device 2 from the list of discovered remote devices 2 that is displayed on the user interface 8 of the medical device 1. The control unit 6 of the medical device 1 then sends identifying information of the selected remote electronic device 2, e.g., the address of the communication module of the remote electronic device 2 that has been selected, to the communication module 3 in step 35, and thereafter at step 36 the control unit 6 instructs the communication module 3 of the medical device 1 to begin pairing with the communication module 4 of the remote electronic device 2 by requesting authentication.

Alternatively, the medical device 1 may not be operable at steps 27-36 to scan for, and select from, potential pairable remote electronic devices 2 in range, and instead the control unit 6 may be operable to control the user interface 8 to request the user to manually provide an identifying information, e.g., a virtual address, to the control unit 6, e.g., via a keypad or other conventional data entry mechanism, of a particular remote electronic device 2 that is to be paired with the medical device 1.

Pairing between the communication module 3 and the communication module 4 begins at steps 36 and 37 respectively, and is conducted on the communications layer 5. The communication modules 3, 4 of the medical device 1 and the remote electronic device 2 are both prompted at steps 38 and 39 respectively to provide a PIN code. Illustratively, the PIN code is a fixed code that is hard-coded on each of the communication modules 3, 4. Alternatively, the PIN code for each module 3, 4 may be stored in a memory of the respective control units 6, 7, or otherwise provided to the communication modules 3, 4 from an external source. The PIN codes may generally comprise any number of alphanumeric characters, purely numeric characters, purely alphabetic characters, purely symbolic characters or any combination thereof. The communication module 3 initiates pairing with the communication module 4 by requesting authentication with the PIN code. In step 40, the communication module 3 sends the pairing result to the control unit 6 of the medical device 1, the pairing result comprising the identity, e.g., the communication address, of the remote electronic device 2 based on the PIN code provided by the control module 4 of the remote electronic device 2. In steps 41, 42, 43 the control unit 6 and the communication module 3 of the medical device 1, and the communication module 4 of the remote electronic device 2, each check if the pairing has been successful, i.e. if the identity, e.g., the communication address, of the other device 2, 1, has been authenticated successfully. On successful authentication, i.e. on successful pairing, the communication modules 3, 4 of the medical device 1 and of the remote electronic device 2 respectively each generate a unique link key or a plurality of link keys and store the link key or keys and the communication address of the other device 2, 1 locally in a memory of the medical device 1 and of the remote device 2, respectively (steps 44 and 45). Illustratively, the local memory in each device 1, 2 in which the link key or keys and the communication address of the other device 2, 1 are stored is a non-volatile memory such that the stored information will be retained in the respective memories until overwritten. Alternatively, the local memory in each device 1, 2 in which the link key or keys and the communication address of the other device 2, 1 are stored may be a volatile memory, in which case the pairing process, including the exchange and storage of the link keys and communication addresses, will be required after device power up.

If the pairing has not been successful in steps 41, 42 and 43, then the control unit of the medical device 1 is operable in step 46 to control the user interface 8 to display a message indicating that the pairing process was not successfully completed, e.g., a message such as "Process not successful" or other message. At step 48, the communication module 3 of the medical device 1 transitions to an idle state, and in step 47 the control unit 6 exits the pairing menu displayed on the user interface 8 of the medical device 1 and powers off the communication module 3. After steps 47 and 48, the pairing process within the medical device 1 ends. In the remote electronic device 2, the communication module 4 reacts to the unsuccessful pairing determination by setting the remote electronic device 2 back into pairable mode, i.e. by returning to step 23, in order to be again discoverable by the medical device 1.

Upon successful pairing and link key storage the communication module 3 of the medical device 1 makes itself wirelessly connectable via the communication layer 5 in step 49. Then in step 50 the communication module 4 of the remote electronic device 2 attempts to establish a wireless connection with the communication module 3 of the medical device 1. A wireless connection via the communications layer 5, using a conventional communication protocol, e.g., BlueTooth® communication protocol or other desired communication protocol, is then actually established in step 51. The medical device 1 and the remote device are then wirelessly connected (item 52), and with the pairing of the medical device 1 and the remote electronic device 2 completed wireless communication between the two devices 1, 2 is then possible via the communication layer 5.

In the pairing process described with reference to FIG. 3, the communication module 4 of the remote electronic device 2 was first put into a pairable mode by the user 12, and the control unit 6 and communication module 3 of the medical device 1 thereafter controlled the pairing process. In alternative embodiments, the communication module 3 of the medical device 1 may instead be put into a pairable mode by the user 12, and the control unit 7 and communication module 4 of the remote electronic device 2 may thereafter control the pairing process. In either case, while the pairing process has been described as occurring between a device that has been put in the pairing mode, e.g., a menu-driven pairing mode, and another device that has been put in a pairable mode, e.g., a discoverable device, by a user 12, this disclosure contemplates embodiments in which a license or certificate is required to put a device in the pairable mode. In such embodiments, the license or certificate would carry a serial number, communication address, a combination thereof or the like which would be required to identify the device for pairing. Alternatively still, such a license or certificate may carry all or part of the PIN code, or information relating to the PIN code, and in this embodiment a device could be put in a pairing mode or be put in a pairable mode, but the pairing process could not be completed without the PIN code or PIN code information.

Figure 4:
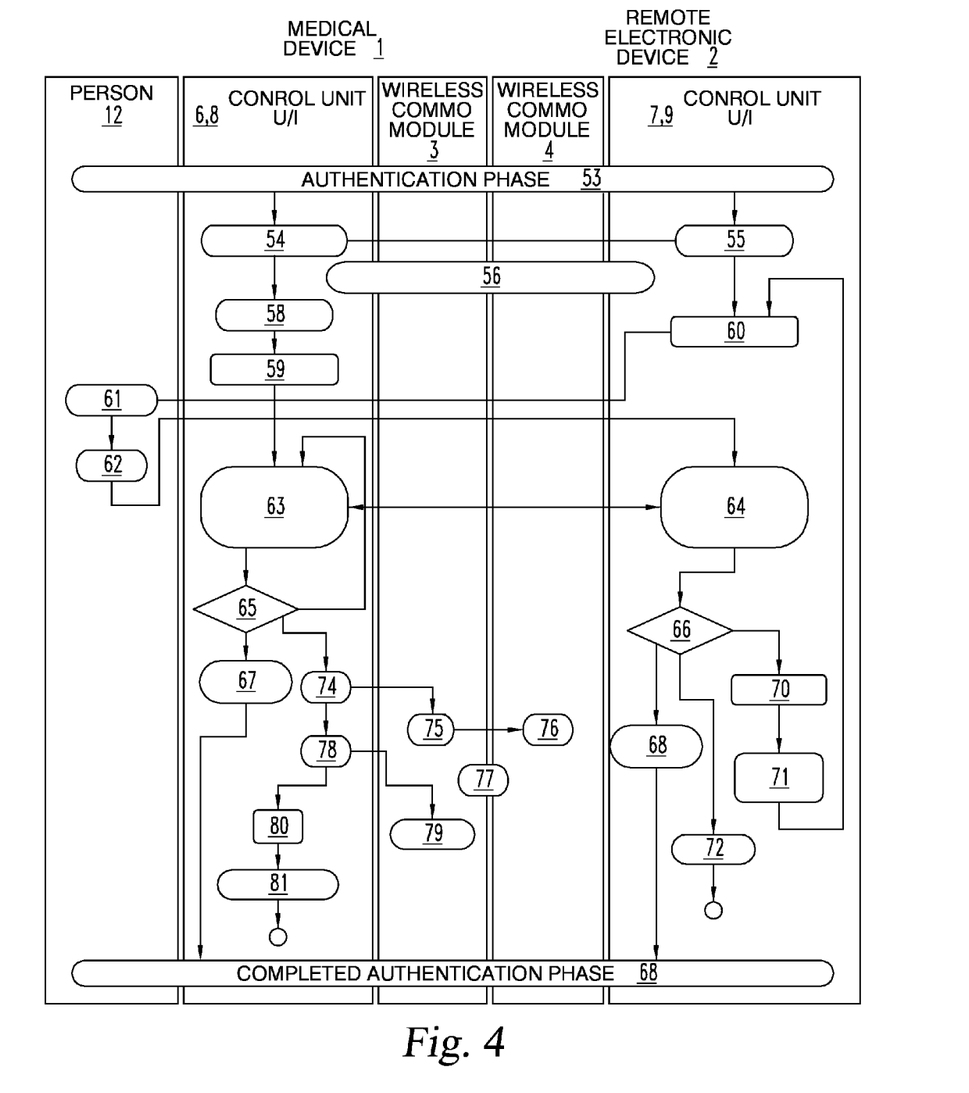
FIG. 4 shows a flowchart of one illustrative embodiment of an authentication process for authenticating the medical device and the remote electronic device following a pairing process such as that illustrated in FIG. 3.

In any case, the pairing and authentication process is continued in step 53 with the authentication phase, the authentication phase being depicted in FIG. 4 as a schematic representation in the form of a flowchart. As with FIG. 3, the various steps/items of the flowchart of FIG. 4 are illustratively carried out by a combination of the user 12, the control unit 6 and user interface 8 of the medical device 1, the communication modules 3 and 4 of the medical device 1 and the remote electronic device 2 respectively and the control unit 7 and user interface 9 of the remote electronic device 2. Item 53 represents the completed pairing phase, and after completion of the pairing phase the control unit 7 of the remote electronic device 2 is able to establish wireless communication with the control unit 6 of the medical device 1 via the transport portion of the security and transport layer 10 in steps 54 and 55. Then, the medical device 1 and the remote electronic device 2 are then connected via the transport portion of the security and transport layer 10 (item 56). Thereafter in step 58, the control unit 6 of the medical device 1 illustratively generates a PIN code and in step 59 the control unit 6 controls the user interface 8 on the medical device 1 to display the generated PIN code. Illustratively, the PIN code may be purely numeric, purely alphabetic, purely symbolic or any combination thereof, and may have any desired character length. In any case, the control unit 6 of the medical device 1 then waits for subsequent authentication of the remote electronic device 2.

In step 60, the control unit 7 of the remote device 2 controls the user interface 9 to display a suitable message prompting the user 12 to provide the PIN code that is currently displayed on the user interface 8 of the medical device 1 to the control unit 7 of the remote electronic device 2, e.g., by manually entering the currently displayed PIN code into the remote electronic device 2 via a keypad or other conventional information input mechanism. In step 61 the user 12 reads the PIN code displayed on the user interface 8 of the medical device 1 and provides in step 62 the PIN code to the control unit 7 of the remote electronic device 2. In alternative embodiments, the PIN code generated by the control unit 6 of the medical device 1 may instead be provided to the control unit 7 of the remote electronic device 2 by a mechanism other than manual entry by the user 12. For example, the PIN code may be exchanged between the two devices 1, 2 via a suitable wireless data exchange mechanism, e.g., RFID or the like, or via a wired connected between input and output data ports of the control unit 7 and the control unit 6 respectively. In other alternate embodiments, the complete PIN code may not be generated solely by the control unit 6 of the medical device 1, and may instead be generated in part by the control unit 6 and in part by the control unit 7 of the remote electronic device 2. In such cases, the control unit 7 may be operable to assemble or otherwise determine the complete PIN code based on the portion of the PIN code generated by the control unit 6 and provided to the control unit 7 via any of the mechanisms described above and also based on the portion of the PIN code generated by the control unit 7. In such cases, the complete PIN code will not be known by the control unit 6 of the medical device 1 until it is wirelessly transmitted, via the communication modules 4 and 3 respectively, by the control unit 7 of the remote electronic device 2 back to the control unit 6 of the medical device 1.

In steps 63 and 64, the control unit 6 of the medical device 1 and the control unit 7 of the remote electronic device 2 check the authentication of the PIN code that was provided to the control unit 7 as described above. For authentication of the PIN code the control unit 6 of the medical device 1 generates a signature from the generated PIN code, for example by applying a symmetric encryption method such as AES, DES, IDEA, Blowfish or other symmetric or non-symmetric encryption method. The control unit 7 of the remote electronic device 2 also generates a signature based on the entered PIN code, for example by applying the same encryption as the medical device 1. The control unit 6 of the medical device 1 attaches the signature to a data packet and sends it to the control unit 7 of the remote electronic device 2 via the communication modules 3, 4 using the transport portion of the security and transport layer 10. The control unit 7 of the remote electronic device 2 then checks if the signature which is attached to the sent data packet is the same as the signature it has generated itself. If the signatures are the same, then authentication of the PIN code has been successful.

The control unit 6 of the medical device 1 then generates one or more strong keys. The control unit 7 of the remote electronic device 2 may request delivery of such one or more strong keys from the medical device 1. In alternative embodiments both devices 1 and 2 may each generate one or more strong keys. In any case, the control unit 6 of the medical device 1 encrypts the one or more strong keys it has generated, for example by applying a symmetric encryption method such as AES, DES, IDEA, Blowfish or other symmetric or non-symmetric encryption method, and sends the one or more encrypted strong keys to the control unit 7 of the remote electronic device 2 via the communication modules 3, 4 using the transport portion of the security and transport layer 10. The control unit 7 of the remote electronic device 2 then decrypts the one or more encrypted strong keys received from the control unit 6 of the medical device 1. Upon successful authentication of the one or more strong keys, the strong key exchange phase is completed. The control units 6 and 7 thereafter use the strong keys to generate and check the signatures for each data packet sent between the devices 1 and 2. The control units 6 and 7 exchange device identification information, e.g., device serial numbers or other device identification codes. Alternatively, the control units 6 and 7 may exchange device identification information at other times during the pairing and authentication process. In any case, other authentication methods can be applied alternatively or additionally to either of the authentication of the PIN code and the authentication of the one or more strong keys.

Figure 5:
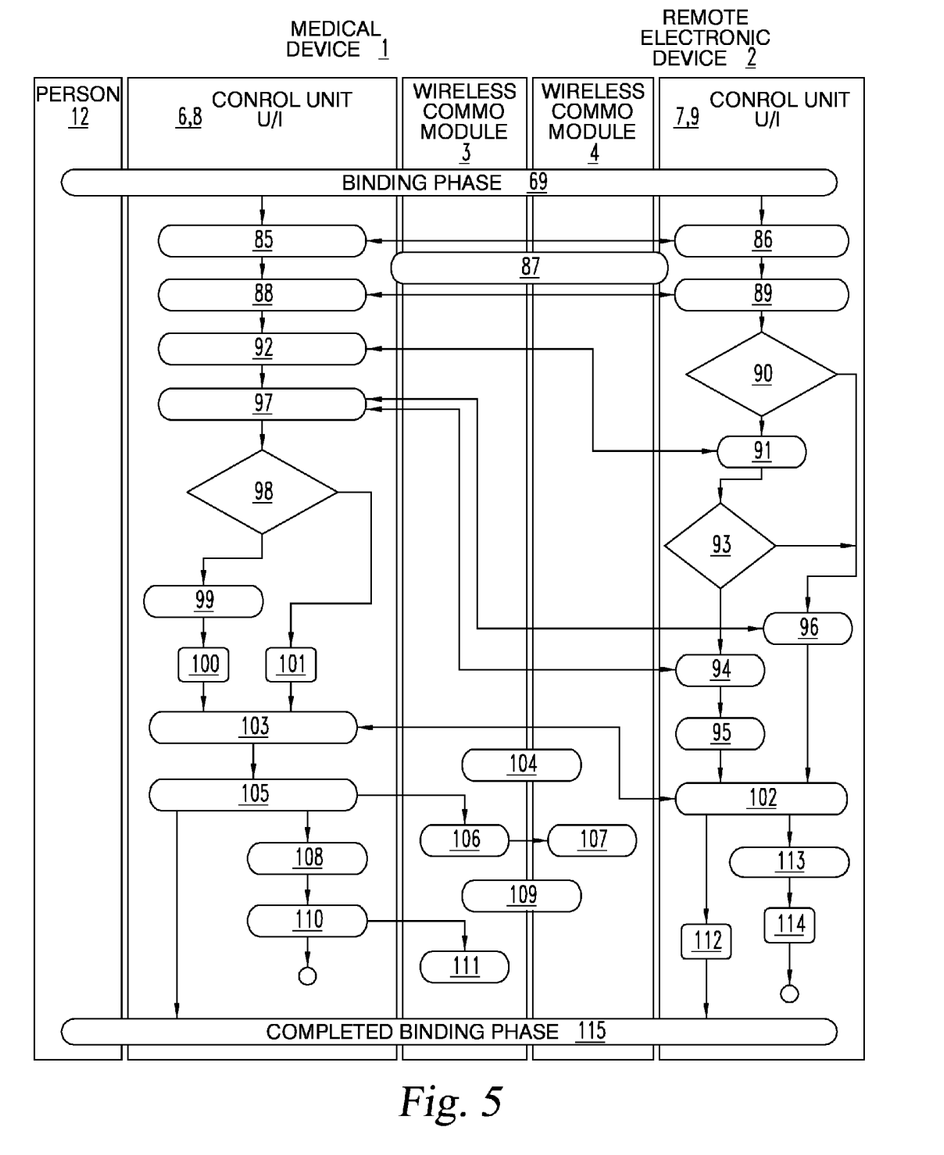
FIG. 5 shows a flowchart of one illustrative embodiment of a binding process that may follow the authentication process of FIG. 4.

Each control unit 6, 7 of the medical device 1 and the remote electronic device 2 respectively checks in steps 65 and 66 if the authentication process performed in steps 63 and 64 has been successful. On successful authentication the medical device 1 and the remote electronic device 2, the control unit 6 and the control unit 7 each store in steps 67 and 68 the one or more strong keys in a memory of the respective device 1, 2. In one embodiment, the memories in which the one or more strong keys are stored are non-volatile. In alternative embodiments, the memories in which the one or more strong keys are stored are volatile, in which case the authentication phase illustrated in FIG. 4 must be executed at each power up of the devices 1, 2. In still other alternative embodiments, the one or more strong keys may be stored in the memory of either device 1, 2 in encrypted form. In any case, the control unit 6 of the medical device 1 and the control unit 7 of the remote electronic device 2 may each also control their respective user interfaces 8, 9 to display a message in steps 67 and 68 indicating that the authentication process has been successful. In some embodiments, such as in embodiments in which the binding phase or process of FIG. 5 is omitted, the control unit 7 of the remote electronic device 2 may also control the user interface 9 at step 68 to prompt the user 12 to restart the remote electronic device 2, and/or the control unit 6 of the medical device 1 may control the user interface 8 to prompt the user 12 to restart the medical device 1, although a restart of the medical device 1 and/or remote electronic device 2 may be omitted in other embodiments.

If at steps 65 and 66 the control units 6 and 7 of the devices 1 and 2 respectively determine that the authentication process was not successful, the control unit 6 of the medical device 1 illustratively loops back to step 63 and the control unit 7 of the remote electronic device 2 illustratively controls the user interface 9 to display at step 70 a message indicating that the wrong PIN code was entered and then controls the user interface 9 to display at step 71 the previously entered PIN code before looping back to step 60. The user 12 then has an opportunity to correct an incorrectly entered PIN code, and the process then proceeds as described above. In an alternate embodiment, step 70 does not advance to step 71 but instead loops back to step 58 where the control unit 6 of the medical device 1 is operable to generate a new PIN code after which the authentication process proceeds as described above.

If at step 66 the control unit 7 of the remote electronic device 2 determines that a power off of the remote electronic device has been requested or a timeout has occurred without user intervention following an unsuccessful authentication attempt, the control unit 7 is operable at step 72 to power off the remote electronic device 2. If at step 65 the control unit 6 of the medical device 1 determines that the user 12 has exited the process or a timeout has occurred after an unsuccessful authentication attempt, the control unit 6 instructs the communication module 3 at step 74 to disconnect from the communication module 4. Thereafter in steps 75 and 76, the communication modules 3 and 4 disconnect from each other, thereby resulting in disconnection of the communications layer 5 (item 77). Following step 74, the control unit 6 instructs the communication module 3 at step 78 to unpair from the communication module 4 of the remote electronic device 2, after which the communication module 3 unpairs from the communication module 4 at step 79. Following step 78, the control unit 6 also illustratively controls the user interface 8 of the medical device 1 at step 80 to display a message indicating that the authentication process was not successful. Thereafter at step 81 the control unit 6 controls the user interface 8 to exit the pairing and authentication menu and to then power off the communication module 3.

In the authentication process described with reference to FIG. 4, the control unit 6 of the medical device 1 generated the PIN code and thereafter the control unit 7 of the remote electronic device 2 controlled authentication of the PIN code entered into the remote electronic device 2 and controlled authentication of one or more strong keys that were generated by the control unit 6. In alternative embodiments, the control unit 7 of the remote electronic device 2 may instead generate the PIN code and the control unit 6 of the medical device 1 may control authentication of the PIN code and thereafter control authentication of the one or more strong keys.

In any case, the pairing and authentication process is continued in step 69 with an optional binding phase, the binding phase being depicted in FIG. 5 as a schematic representation in the form of a flowchart. The various steps/items of the flowchart of FIG. 5 are illustratively carried out by a combination of the control unit 6 and user interface 8 of the medical device 1, the communication modules 3 and 4 of the medical device 1 and the remote electronic device 2 respectively and the control unit 7 and user interface 9 of the remote electronic device 2. Item 69 represents the completed authentication phase, and after completion of the authentication phase the control unit 7 of the remote electronic device 2 is able to establish wireless communication with the control unit 6 of the medical device 1 via the application layer 11 in steps 85 and 86. The medical device 1 and the remote electronic device 2 are then connected via the application layer 11 (item 87). Thereafter in steps 88 and 89, the control unit 7 of the remote electronic device 2 illustratively requests the service version of one operating mode of the remote electronic device 2 from the control unit 6 of the medical device 1. In this embodiment, a version number or code of instructions that are stored in a memory of the remote electronic device 2 and executable by the control unit 7 to operate the remote electronic device 2 in accordance with the one operating mode is stored in the memories of the medical device 1 and the remote electronic device 2. The control unit 6 of the medical device 1 is operable at step 88 to provide the version number or code of the one operating mode of the remote electronic device 2 to the control unit 7 of the remote electronic device 2, which is then operable at step 90 to compare the sent version number or code with the corresponding version number or code stored in the memory of the remote electronic device 2. If the two version numbers or codes match, the binding process advances to steps 91 and 92.

In steps 91 and 92, the control unit 7 of the remote electronic device 2 illustratively requests the service version of another operating mode of the remote electronic device 2 from the control unit 6 of the medical device 1. As with the previous operating mode, a version number or code of instructions that are stored in a memory of the remote electronic device 2 and executable by the control unit 7 to operate the remote electronic device 2 in accordance with the another operating mode is stored in the memories of the medical device 1 and the remote electronic device 2. The control unit 6 of the medical device 1 is operable at step 92 to provide the version number or code of the another operating mode of the remote electronic device 2 to the control unit 7 of the remote electronic device 2, which is then operable at step 93 to compare this sent version number or code with the corresponding version number or code stored in the memory of the remote electronic device 2. If these two version numbers or codes match, the binding process advances to step 94 where the control unit 7 of the remote electronic device 2 generates a pass code, and thereafter at step 95 the control unit 7 sets a binding flag in a memory of the remote electronic device 2. In one embodiment, the control unit 7 is operable to set the binding flag in a non-volatile memory of the remote electronic device 2. Alternatively, the control unit 7 may be operable at step 95 to set the binding flag in a volatile memory of the remote electronic device 2, in which case the binding phase of FIG. 5 must be repeated with each power up of the remote electronic device 2. On the other hand, if either of steps 90 or 93 result in a mismatch of the version numbers or codes, the control unit 7 of the remote electronic device 2 generates a fail code at step 96.

The pass/fail information is sent by the control unit 7 of the remote electronic device 2 in steps 94 and 96 to the control unit 6 of the medical device 1 via the application layer 11, which is received by the control unit 6 in step 97. Thereafter in step 98, the control unit 6 of the medical device 1 processes the pass/fail information and if the pass code was generated in step 94 the control unit 6 sets a binding flag in a memory of the medical device 1 in step 99 and thereafter controls the user interface 8 in step 100 to display a message indicating that the binding phase was successful. In one embodiment, the control unit 6 is operable to set the binding flag in a non-volatile memory of the medical device 1. Alternatively, the control unit 7 may be operable in step 99 to set the binding flag in a volatile memory of the medical device 1, in which case the binding phase of FIG. 5 must be repeated with each power up of the medical device 1. If, on the other hand, the control unit 6 of the medical device 1 determines in step 98 that the fail code was generated in step 96 the control unit 6 controls the user interface 8 in step 101 to display a message indicating that the binding phase was not successful.

Following either of steps 95 and 96, the control unit 7 of the remote electronic device 2 is operable in step 102 to instruct the control unit 6 of the medical device 1 to disconnect the application layer 11, and in steps 102 and 103 the control units 6 and 7 together disconnect the application layer 11 (item 104). Following step 103, the control unit 6 of the medical device 1 is operable in step 105 to instruct the communication module 3 to disconnect from the communication module 4 of the remote electronic device 2. Thereafter in steps 106 and 107, the communication modules 3 and 4 disconnect from each other, thereby resulting in disconnection of the communications layer 5 (item 109). Also following step 105, the control unit 6 is operable in step 108 to remove the authentication data, e.g., the one or more strong keys, from the memory of the medical device 1. Thereafter in step 110 the control unit 6 of the medical device 1 instructs the communication module 3 to unpair from the communication module 4 of the remote electronic device 2, after which the communication module 3 unpairs from the communication module 4 at step 111.

If the pass code was set at step 94, the control unit 7 of the remote electronic device 2 is operable following step 102 to control the user interface 9 to display in step 112 a message indicating that the binding process was successful. If, on the other hand, the fail code was set in step 96, the control unit 7 of the remote electronic device 2 is operable following step 102 to remove in step 113 the authentication data, e.g., the one or more strong keys, from the memory of the remote electronic device 2. Thereafter in step 114, the control unit 7 is operable to control the user interface 9 of the remote electronic device 2 to display a message indicating that the binding process was not successful.

If the binding process of FIG. 5 is successfully completed, the process advances to step 115 which indicates that the medical device 1 and the remote electronic device 2 are authenticated for future use and communication and connection via the application layer 11 after power up. For future communication the one or more strong keys are used, which is stored in the memories of the medical device 1 and the remote electronic device 2.

In the binding phase of FIG. 5 as just described, the control unit 7 of the remote electronic device 2 was operable to compare service version numbers or codes for two different operating modes of the remote electronic device 2. In one example embodiment, which should not be considered limiting in any way, the two different operating modes may be a command mode in which the remote electronic device 2 computes a recommended therapy to be administered by the medical device, e.g., an amount of a drug to be infused or otherwise delivered, and a remote terminal mode in which the remote electronic device 2 is operable to control the operation of the medical device 1 in real time. It will be understood that the binding phase illustrated in FIG. 5 may alternatively be configured to compare service version numbers or codes for more, fewer and/or other operating modes of the remote electronic device, and modifications to the illustrated process to accomplish this would be a mechanical step for a person of ordinary skill in the art. It will be further understood that information exchanged between the medical device 1 and the remote electronic device 2 via the application layer 11 during the binding phase may alternatively or additionally be encrypted using any conventional encrypting techniques.

In the binding phase described with reference to FIG. 5, the control unit 7 of the remote electronic device 2 controlled comparisons of the service version numbers or codes and setting of the corresponding pass and fail codes. In alternative embodiments, the control unit 6 of the medical device 1 may instead control the comparisons of the service version numbers or codes and setting of the corresponding pass and fail codes.

It will be understood that the pairing and authentication process described herein will typically be initiated before the first connection between a medical device 1 and a remote electronic device 2 in order to enable secure communication between the medical device 1 and the remote electronic device 2. The process will also typically be performed upon replacement of either the medical device 1 or the remote electronic device 2.

While the invention has been illustrated and described in detail in the foregoing drawings and description, the same is to be considered as illustrative and not restrictive in character, it being understood that only illustrative embodiments thereof have been shown and described and that all changes and modifications that come within the spirit of the invention are desired to be protected. For example, throughout the pairing and authentication process described herein, the control unit 6 of the medical device 1 controls portions of the process and is therefore the master in such portions of the process while the control unit 7 of the remote electronic device 2 is the slave in such portions of the process, and the control unit 7 of the remote electronic device 2 controls other portions of the process and is therefore the master in such other portions of the process while the control unit 6 is the slave in such other portions of the process. As discussed hereinabove, this disclosure contemplates alternate embodiments in which the master/slave relationships of the control units 6 and 7 are reversed in whole or in part during one or more phases of the pairing and authentication process.

What is claimed is:

1. A method for establishing secure wireless communications between a Bluetooth medical device and a Bluetooth remote electronic device using application layer security data packet message authentication, comprising:
   creating and exchanging a personal identification number (PIN) code between the Bluetooth medical device and the Bluetooth remote electronic device for pairing comprising:
      generating the PIN code by the Bluetooth medical device;
      displaying the PIN code generated by the Bluetooth medical device on the Bluetooth medical device; and
      instructing via a display of the Bluetooth remote electronic device, manual input of the at least the portion of the generated PIN code displayed on the Bluetooth medical device into the Bluetooth remote electronic device for security;
      sending by the Bluetooth remote electronic device the PIN Code from the Bluetooth remote electronic device to the Bluetooth medical device;
      receiving and confirming receipt of the PIN code by the Bluetooth remote electronic device sent from the Bluetooth medical device;
   authenticating the PIN code, without using a link key, comprising:
      generating first signature by the Bluetooth medical device from the PIN code using a symmetric encryption technique;
      generating second signature by the Bluetooth remote electronic device from the entered PIN code using the symmetric encryption technique;
      attaching the first signature to first data packet by the Bluetooth medical device;
      sending the first data packet with the first signature by the Bluetooth medical device to the Bluetooth remote electronic device using a transport layer;
      authenticating the PIN code when the first signature attached to the first data packet sent by the Bluetooth medical device is the same as the second signature generated by the Bluetooth remote electronic device;
   generating a strong key, that is not derived from the link key, by the Bluetooth medical device for the purpose of secure key exchange comprising:
      encrypting the strong key by the Bluetooth medical device that generated the strong key by applying the PIN code as an encryption key to a symmetric encryption technique;
      sending the strong key encrypted by the Bluetooth medical device to the Bluetooth remote electronic device;
      decrypting the strong key by the Bluetooth remote electronic device that had been encrypted and sent by the Bluetooth medical device;
   authenticating application layer signatures from a data packet comprising:
      generating third signature by the Bluetooth medical device from the strong key using the symmetric encryption technique;
      generating fourth signature by the Bluetooth remote electronic device from the strong key using the symmetric encryption technique;
      attaching the third signature to the data packet by the Bluetooth medical device;
      sending the data packet with the third signature by the Bluetooth medical device to the Bluetooth remote electronic device using a application layer;
      authenticating the application layer signature when the third signature attached to the data packet sent by the Bluetooth medical device is the same as the fourth signature generated by the Bluetooth remote electronic device; and
      refusing the data packet when the third signature attached to the data packet sent by the Bluetooth medical device is not the same as the fourth signature generated by the Bluetooth remote electronic device;
   performing a binding phase comprising:
      sending service versions of all operating modes of the Bluetooth remote electronic device by the Bluetooth medical device to the Bluetooth remote electronic device;
      upon a determination by the Bluetooth medical device that the sent service versions are compatible with corresponding service versions stored in the memory of the Bluetooth remote electronic device, storing a pass lag in a memory of the Bluetooth medical device and in a memory of the Bluetooth remote electronic device, and
      upon a determination by the Bluetooth medical device that at least one of the sent service versions is not compatible with a corresponding one of the service versions stored in the memory of the Bluetooth remote electronic device, removing the at least one strong key from the memory of the Bluetooth medical device and from the memory of the Bluetooth remote electronic device.

* * * * *